United States Patent [19]

Heeres

[11] 4,101,664
[45] * Jul. 18, 1978

[54] 1-(2-AR-4-ARYLOXYMETHYL-1,3-DIOXO-LAN-2-YLMETHYL)-IMIDAZOLES

[75] Inventor: Jan Heeres, Vosselaar, Belgium

[73] Assignee: Janssen Pharmaceutica N.V., Beerse, Belgium

[*] Notice: The portion of the term of this patent subsequent to Feb. 3, 1993, has been disclaimed.

[21] Appl. No.: 732,828

[22] Filed: Oct. 15, 1976

Related U.S. Application Data

[63] Continuation-in-part of Ser. No. 619,863, Oct. 6, 1975, abandoned, which is a continuation-in-part of Ser. No. 544,157, Jan. 27, 1975, Pat. No. 3,936,470.

[51] Int. Cl.$^2$ .................... A61K 31/33; C07D 405/06
[52] U.S. Cl. .................... 424/273 R; 260/340.9 R; 548/336; 548/341
[58] Field of Search .................... 260/309; 424/273; 548/336

[56] References Cited

U.S. PATENT DOCUMENTS

| | | | |
|---|---|---|---|
| 3,575,999 | 4/1971 | Godefroi et al. | 260/309 |
| 3,717,655 | 2/1973 | Godefroi et al. | 260/309 |
| 3,936,470 | 2/1976 | Heeres | 260/309 |

*Primary Examiner*—Natalie Trousof
*Attorney, Agent, or Firm*—Salvatore R. Conte

[57] ABSTRACT

1-(2-Ar-4-aryloxymethyl-1,3-dioxolan-2-ylmethyl)-imidazoles useful as antifungal and antibacterial agents.

4 Claims, No Drawings

1-(2-AR-4-ARYLOXYMETHYL-1,3-DIOXOLAN-2-YLMETHYL)-IMIDAZOLES

CROSS-REFERENCE TO RELATED APPLICATIONS

This is a continuation-in-part of my copending application, Ser. No. 619,863, filed Oct. 6, 1975, now abandoned, which in turn is a continuation-in-part of my application Ser. No. 544,157, filed Jan. 27, 1975, now issued as U.S. Pat. No. 3,936,470.

PRIOR ART

In U.S. Pat. Nos. 3,575,999 and 3,717,655 are described some 1-(2-aryl-1,3-dioxolan-2-ylmethyl)imidazoles. The compounds of this invention differ from the foregoing essentially by the nature of the aryloxymethyl substituent, present in the 4-position of the dioxolane group.

DESCRIPTION OF THE INVENTION:

This invention relates to novel imidazole derivatives having the formula:

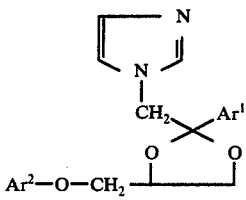

and the therapeutically acceptable acid addition salts thereof, wherein:

$Ar^1$ is a member selected from the group consisting of naphthalenyl, thienyl, halothienyl, nitrophenyl, cyanophenyl, lower alkylhalophenyl and lower alkyloxyhalophenyl; and $Ar^2$ is a member selected from the group consisting of phenyl, substituted phenyl, naphthalenyl and halonaphthalenyl, and wherein said substituted phenyl is phenyl having from 1 to 3 substituents independently selected from the group consisting of halo, lower alkyl, lower alkyloxy, cyano, phenyl and phenylmethyl.

As used herein, "lower alkyl" is meant to include straight and branch chained hydrocarbon radicals having from 1 to 6 carbon atoms, such as, for example, methyl, ethyl, propyl, butyl, 1-methylethyl, 1,1-dimethylethyl, pentyl, hexyl and the like alkyls; and the term "halo" refers to halogens of atomic weight less than 127, i.e., fluoro, chloro, bromo and iodo.

The compounds of formula (I) are conveniently prepared by reacting imidazole (II) with an appropriate reactive ester of formula (III) wherein $Ar^1$ and $Ar^2$ are as previously defined and wherein W is a reactive ester function, such as, halo, (4-methylphenyl)sulfonyloxy, methylsulfonyloxy and the like. Preferred reactive esters are halides and more particularly bromides and chlorides.

The reaction of imidazole with the reactive ester (III) may be carried out by bringing the reactants in contact with each other in an appropriate organic solvent, such as, for example, N,N-dimethylformamide or N,N-dimethylacetamide. It is appropriate to use an excess of imidazole or to add to the reaction mixture an appropriate base such as sodium or potassium carbonate or hydrogencarbonate. The use of an excessive amount of imidazole is however preferred. Further it is advantageous to conduct the reaction in the presence of a metal iodide, such as, for example, sodium or potassium iodide. Somewhat elevated temperatures may be employed to enhance the rate of the reaction and most conveniently the reaction is carried out at the reflux temperature of the reaction mixture.

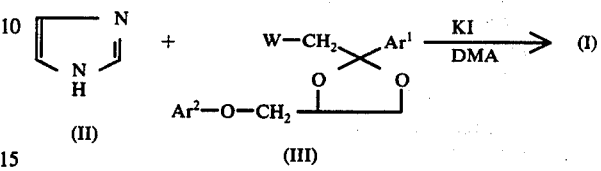

An additional method of preparing the compounds of formula (I) is by the ketalization of an appropriate aroylmethylimidazole of formula (IV) wherein $Ar^1$ has the same meaning as assigned to it previously, with an appropriate diol of formula (V) wherein $Ar^2$ is as previously defined.

Said ketalization reaction may be carried out following methodologies analogous to those described in the literature, e.g., for the preparation of 2-bromomethyl-2,4-diphenyl-1,3-dioxolane [Synthesis, 1974 (I), 23].

In a preferred manner of carrying out the reaction both reactants are refluxed together for several hours with azeotropic water removal in an appropriate organic solvent; preferably in the presence of a simple alcohol, such as, for example, ethanol, propanol, butanol, pentanol and the like, and in the presence of an appropriate strong acid such as 4-methylbenzenesulfonic acid. Suitable organic solvents are, for example, aromatic hydrocarbons, such as, benzene, methylbenzene, dimethylbenzene and the like and saturated hydrocarbons such as cyclohexane.

The foregoing reaction may be illustrated as follows:

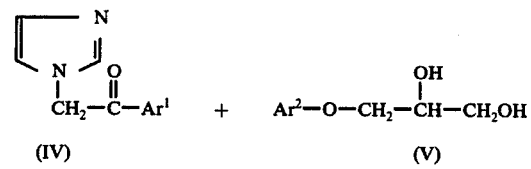

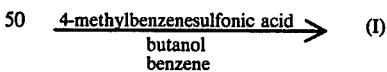

The reaction products obtained in the foregoing preparations may be isolated from the medium and, if necessary, further purified according to methodologies known in the art, such as, for example, extraction, trituration, crystallization, chromatography, etc.

The imidazole derivatives of formula (I), obtained in base form in the foregoing preparations, may be converted to their therapeutically useful acid addition salts by reaction with an appropriate acid, as, for example, an inorganic acid such as hydrohalic acid, i.e., hydrochloric, hydrobromic or hydroiodic acid; sulfuric, nitric or thiocyanic acid; a phosphoric acid; an organic acid such as acetic, propanoic, hydroxyacetic, α-hydroxypropanoic, 2-oxopropanoic, ethanedioic, propanedioic, 1,4-butanedioic, (Z)-2-butenedioic, (E)-2-butenedioic, 2-hydroxy-1,4-butanedioic, 2,3-dihydroxy-1,4-butanedioic, 2-hydroxy-1,2,3-propanetricarboxylic, benzoic, 3-phenylpropenoic, α-hydroxybenzeneacetic, methanesulfonic, ethanesulfonic, 2-hydroxyethanesulfonic, 4-methylbenzenesulfonic, 2-hydroxybenzoic, 4-amino-2-hydroxybenzoic, 2-phenoxybenzoic or 2-acetyloxybenzoic acid. The salts are in turn converted to the corresponding free bases in the usual manner, e.g., by reaction with alkali such as sodium or potassium hydroxide.

The intermediates of formula (III) may be prepared by subjecting an appropriate ketone of formula (VI), wherein $Ar^1$ and W are as previously defined to a ketalization reaction with an appropriate diol of formula (V) in the same manner as described hereinbefore for the preparation of the compounds (I) starting from (IV) and (V).

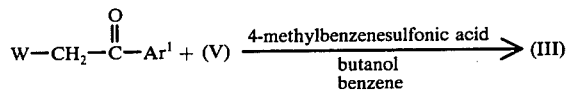

Alternatively the intermediates of formula (III) are conveniently prepared by transketalization of a ketal derivative of a ketone of formula (VI) such as, for example, a lower alkyl ketal or a cyclic lower alkylene ketal, with a diol of formula (V) under similar conditions to those described hereinbefore for the direct ketalization. The lower alkyl and cycliclower alkylene ketals used herein as starting materials are easily obtained by ketalization of a ketone of formula (VI) with a lower alkanol or alkanediol according to methodologies known in the art. A number of such compounds and methods of preparing the same are described in U.S. Pat. No. 3,575,999.

The intermediates of formula (III) are deemed to be novel and as useful intermediates herein they constitute an additional feature of this invention.

A number of the precursor diols of formula (V) are known and they may all be prepared according to known procedures as described in the literature.

The precursor aryl ketones of formula (VI) are generally known and may be prepared according to known procedures as described in the literature. Bromides are, for example, easily obtained by the bromination of the corresponding methyl aryl methanone with bromine.

The aroylmethyl substituted imidazoles of formula (IV), a number of which are described in U.S. Pat. No. 3,658,813, are conveniently prepared by the reaction of (VI) with imidazole in an analogous manner as previously described for the preparation of the compounds (I) starting from imidazole and (III).

From formula (I) it is evident that the compounds of this invention have two asymmetric carbon atoms in their structures, namely those located in the 2- and 4-position of the dioxolane nucleus, and consequently they exist under different stereochemical optical isomeric forms. The stereochemical optical isomeric forms of (I) and the therapeutically active acid addition salts thereof are intended to be within the scope of this invention.

The diastereomeric racemates of (I), denoted as cis and trans forms respectively, according to the rules described in "Naming and Indexing of Chemical Substances for Chemical Abstracts during the 9th Collective Period (1972-1976)", published in C.A. 1972, 76, Index Guide Section IV, p. 85, may be obtained separately by conventional methods. Appropriate methods which may advantageously be employed therefore include, for example, selective crystallization and column-chromatography. For a number of compounds the stereochemical configuration was experimentally determined. In the remaining cases it is conventionally agreed to designate the stereochemical form which is first isolated as "A" and the second as "B", without further reference to the actual stereochemical configuration.

Since the asymmetric carbon atoms are already present in the intermediates (III) it is also possible to separate cis and trans forms, for generally "A" and "B" forms at this stage, whereupon the corresponding forms of (I) may be obtained after reaction of the foregoing with imidazole as previously described. The separation of cis and trans forms of (III) may be performed by conventional methods as described hereinbefore for the separation of the compounds (I) into their cis and trans forms.

It is evident that the cis and trans diastereomeric racemates may be further resolved into their optical isomers, cis (+), cis (−), trans (+) and trans (−) by the application of methodologies known to those skilled in the art.

The compounds of formula (I) and the acid addition salts thereof are useful agents in combatting fungi and bacteria. As such they are valuable in the treatment of human beings, animals and plants suffering from pathogenic microorganisms and in the destruction of microorganisms on materials.

The broad spectrum of antifungal and antibacterial activity of the compounds of formula (I) is clearly illustrated by the experimental data presented hereafter. The compounds in the tables are not listed for the purpose of limiting the invention thereto, but only in order to exemplify the useful properties of all the compounds within the scope of formula (I).

The test for antifungal activity was performed using Sabouraud's liquid medium in test tubes each containing 4.5 ml of liquid medium, autoclaved at 120° C for 15 minutes. The substances were dissolved in 50% ethanol at a concentration of 20mg/ml and subsequently diluted with sterile distilled water to a concentration of 10mg/ml. Successive decimal dilutions were then made with distilled water to give a series of stock solutions. To each tube containing 4.5 ml of Sabouraud's liquid medium was added 0.5 ml of one of the stock solutions to give a concentration of the drug under investigation of 100 μg, 10 μg, 1 μg or 0.1 μg per ml of medium. Filamentous fungi were incubated at 25° C for 2 - 3 weeks. A square block of side 2 mm. was excised and inoculated into the liquid medium. A three-day old culture on Sabouraud's liquid medium was used for yeasts, and the inoculum was 0.05 ml per tube. All the cultures were incubated at 25° C for 14 days. The final readings were taken after two weeks and are summarized in the Tables I as follows:

++++ = complete inhibition of growth at 0.1 μg/ml
+++ = complete inhibition of growth at 1 μg/ml
++ = complete inhibition of growth at 10 μg/ml
+ = complete inhibition of growth at 100 μg/ml
0 = no effect, i.e. growth was observed at the highest concentration tested (100 μg/ml).

In a first screening the drugs under investigation were tested against the following 9 fungi:
1. Microsporum canis (M. c. in the tables)
2. Ctenomyces mentagrophytes (Ct. m. in the tables)

3. Trichophyton rubrum (Tr. r. in the tables)
4. Phialophora verrucosa (Ph. v. in the tables)
5. Cryptococcus neoformans (Cr. n. in the tables)
6. Mucor species (Muc. in the tables)
7. Aspergillus fumigatus (A. f. in the tables)
8. Sporotrichum schenckii (Sp. s. in the tables)
9. Saprolegnia species (Sap. in the tables).

Bactericidal tests were performed on cultures on phenol red dextrose broth Difco medium. The same decimal dilution techniques as described herebefore were used. The inoculum consisted of a platinum loop (5mm. diameter) from a 24 hour broth culture. 48 Hours after incubation, subcultures were made from each culture and for the assessment of the bactericidal activity of the drugs under investigation the presence or absence of growth after 7 days incubation was scored as described above.

The substances were tested against the following gram-positive bacilli and cocci:
1. Erysipelothrix insidiosa (E. ins. in the table),
2. Staphylococcus hemolyticus (Staph. in table), and
3. Streptococcus pyogenes (Strept. in the table). The results are summarized in Table II.

active ingredient in a solvent or a solid, semi-solid or liquid diluent or carrier, and, in addition, it provides an effective method of combatting fungus or bacterial growth by use of an effective anti-fungal or anti-bacterial amount of such ketals (I) or salts thereof. The subject compounds can be used in suitable solvents or diluents, in the form of emulsions, suspensions, dispersions or ointments, on suitable solid or semi-solid carrier substances, in ordinary or synthetic soaps, detergents or dispersion media, if desired, together with other compounds having arachnicidal, insecticidal, ovicidal, fungicidal and/or bactericidal effects, or together with inactive additives.

Solid carrier substances which are suitable for the preparation of compositions in powder form include various inert, porous and pulverous distributing agents of inorganic or organic nature, such as, for example, tricalcium phosphate, calcium carbonate, in the form of prepared chalk or ground limestone, kaolin, bole, bentonite, talcum, kieselguhr and boric acid; powdered cork, sawdust, and other fine pulverous materials of vegetable origin are also suitable carrier substances.

The active ingredient is mixed with these carrier

TABLE I
ANTIFUNGAL ACTIVITY

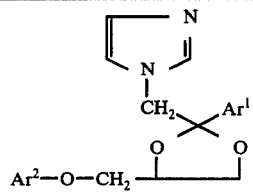

| | | | ANTIFUNGAL ACTIVITY | | | | | | | | |
|---|---|---|---|---|---|---|---|---|---|---|---|
| $Ar^1$ | $Ar^2$ | Isomer | M. c. (1) | Ct. m. (2) | Tr. r. (3) | Ph. v. (4) | Cr. n. (5) | Muc. (6) | A. f. (7) | Sp. s. (8) | Sap. (9) |
| 2-$CH_3$-4-Cl—$C_6H_3$ | 4-Br—$C_6H_4$ | A | +++ | +++ | +++ | + | +++ | ++ | +++ | +++ | ++ |
| 2-$CH_3$-4-Br—$C_6H_3$ | 4-Br—$C_6H_4$ | cis | +++ | +++ | +++ | + | +++ | + | ++ | +++ | ++ |
| 3-$NO_2$—$C_6H_4$ | 4-Br—$C_6H_4$ | cis | 0 | ++++ | ++++ | 0 | 0 | 0 | 0 | 0 | 0 |
| 4-CN—$C_6H_4$ | 4-Br—$C_6H_4$ | cis | ++++ | ++++ | ++++ | 0 | + | 0 | + | 0 | 0 |
| 3-Br-4-$CH_3$—$C_6H_3$ | 4-Br—$C_6H_4$ | cis | ++ | +++ | +++ | 0 | 0 | 0 | + | 0 | 0 |
| 2-Cl-4-$OCH_3$—$C_6H_3$ | 4-($C_6H_5$)—$C_6H_4$ | cis | 0 | ++ | 0 | +++ | 0 | 0 | 0 | 0 | 0 |
| 5-Cl-2-thienyl | 4-($C_6H_5$)—$C_6H_4$ | cis | 0 | ++++ | ++++ | 0 | 0 | 0 | 0 | 0 | 0 |
| 2-thienyl | 4-($C_6H_5$)—$C_6H_4$ | trans | 0 | ++++ | 0 | 0 | 0 | 0 | 0 | 0 | 0 |

TABLE II
BACTERIOSTATIC AND BACTERIOCIDAL ACTIVITY

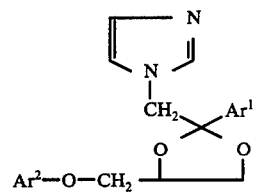

| | | | Bacteriostatic activity | | | Bacteriocidal activity | | |
|---|---|---|---|---|---|---|---|---|
| $Ar^1$ | $Ar^2$ | Isomer | E. ins. | Staph. | Strept. | E. ins. | Staph. | Strept. |
| 2-$CH_3$-4-Cl—$C_6H_3$ | 4-Br—$C_6H_4$ | A | +++ | ++ | +++ | ++ | + | +++ |
| 2-$CH_3$-4-Br—$C_6H_3$ | 4-Br—$C_6H_4$ | cis | +++ | ++ | +++ | +++ | + | +++ |
| 3-$NO_2$—$C_6H_4$ | 4-Br—$C_6H_4$ | cis | >+++ | 0 | ++ | >+++ | 0 | ++ |
| 4-CN—$C_6H_4$ | 4-Br—$C_6H_4$ | cis | ++ | + | >+++ | + | + | >+++ |
| 3-Br-4-$CH_3$—$C_6H_3$ | 4-Br—$C_6H_4$ | cis | +++ | + | +++ | +++ | + | +++ |
| 2-Cl-4-$OCH_3$—$C_6H_3$ | 4-($C_6H_5$)—$C_6H_4$ | cis | +++ | 0 | +++ | +++ | 0 | +++ |
| 5-Cl-2-thienyl | 4-($C_6H_5$)—$C_6H_4$ | cis | >+++ | 0 | >+++ | >+++ | 0 | >+++ |
| 2-thienyl | 4-($C_6H_5$)—$C_6H_4$ | trans | + | 0 | ++ | 0 | 0 | + |
| 2-naphthalenyl | 4-($C_6H_5$)—$C_6H_4$ | trans | +++ | + | ++ | + | 0 | + |

In view of the aforementioned antifungal and antibacterial activities this invention provides valuable compositions comprising the subject 1,3-dioxolan-2-ylmethyl imidazoles (I) or the acid addition salts thereof as the substances, for example, by being ground therewith; alternatively, the inert carrier substance is impregnated with a solution of the active component in a readily volatile solvent and the solvent is thereafter eliminated by heating or by filtering with suction at reduced pressure. By adding wetting and/or dispersing agents, such pulverous preparations can also be made readily wettable with water, so that suspensions are obtained.

Inert solvents used for the production of liquid preparations should preferably not be readily inflammable and should be as far as possible odorless and as far as possible non-toxic to warm-blooded animals or plants in the relevant surroundings. Solvents suitable for this purpose are high-boiling oils, for example, of vegetable origin, and lower-boiling solvents with a flash point of at least 30° C., such as, for example, polyethylene glycols, isopropanol, dimethylsulfoxide, hydrogenated naphthalenes and alkylated naphthalenes. It is, of course, also possible to use mixtures of solvents. Solutions can be prepared in the usual way, if necessary, with assistance of solution promotors. Other liquid forms which can be used consist of emulsions or suspensions of the active compound in water or suitable inert solvents, or also concentrates for preparing such emulsions, which can be directly adjusted to the required concentration. For this purpose, the active ingredient is, for example, mixed with a dispersing or emulsifying agent. The active component can also be dissolved or dispersed in a suitable inert solvent and mixed simultaneously or subsequently with a dispersing or emulsifying agent.

It is also possible to use semi-solid carrier substances of a cream ointment, paste or waxlike nature, into which the active component can be incorporated, if necessary, with the aid of solution promotors and/or emulsifiers. Vaseline and other cream bases are examples of semi-solid carrier substances.

Furthermore, it is possible for the active component to be used in the form of aerosols. For this purpose, the active component is dissolved or dispersed, if necessary, with the aid of suitable inert solvents as carrier liquids, such as difluorodichloromethane, which at atmospheric pressure boils at a temperature lower than room temperature, or in other volatile solvents. In this way, solutions under pressure are obtained which, when sprayed, yield aerosols which are particularly suitable for controlling or combatting fungi and bacteria, e.g., in closed chambers and storage rooms, and for application to vegetation for eradicating or for preventing infections by fungi or bacteria.

The subject compounds and compositions thereof can be applied by conventional methods. For example, a fungus or bacterial growth or a material to be treated or to be protected against attack by fungus or bacterium can be treated with the subject compounds and the compositions thereof by dusting, sprinkling, spraying, brushing, dipping, smearing, impregnating or other suitable means.

When the subject compounds are employed in combination with suitable carriers, e.g., in solution, suspension, dust, powder, ointment, emulsion, and the like forms, a high activity over a very high range of dilution is observed. For example, concentrations of the active ingredient ranging from 0.1 – 10 percent by weight, based on the weight of composition employed, have been found effective in combatting fungi or bacteria. Of course, higher concentrations may also be employed as warranted by the particular situation.

The following examples are intended to illustrate, but not to limit, the scope of the present invention. Unless otherwise stated, all parts are by weight.

EXAMPLE I

To a stirred and hot (50° C) solution of 64 parts of 1-(3-bromo-4-methylphenyl)-1-ethanone in 160 parts of 1-butanol are added dropwise, during a 1 hour-period, 48 parts of bromine without external heating. After stirring for 1 hour at room temperature, there are added successively 21.7 parts of 1,2-ethanediol, 6 parts of 4-methylbenzenesulfonic acid and 720 parts of benzene and the whole is stirred and refluxed overnight with water-separator. The reaction mixture is evaporated and the residue is taken up in 2,2'-oxybispropane. The resulting solution is washed successively once with a diluted sodium hydroxide solution and three times with water, dried, filtered and evaporated. The residue is distilled, yielding 57 parts (57%) of 2-(bromomethyl)-2-(3-bromo-4-methylphenyl)-1,3-dioxolane; bp. 126°–130° C. at 0.1 mm. pressure.

EXAMPLE II

Following the procedure of Example I and using equivalent amounts of the appropriate starting materials, the following dioxolanes are prepared:
2-(bromomethyl)-2-(4-chloro-2-methylphenyl)-1,3-dioxolane; and
2-(bromomethyl)-2-(2-chloro-4-methoxyphenyl)-1,3-dioxolane; mp. 53° C.

EXAMPLE III

To a stirred solution of 112 parts of 4-(2-bromoacetyl)-benzonitrile in 320 parts of butanol are added 5 parts of 4-methylbenzenesulfonic acid and 360 parts of benzene. Then there are added dropwise 46.5 parts of 1,2-ethanediol. Upon completion, sitrring is continued for 4 hours at reflux. The reaction mixture is evaporated. The oily residue is crystallized from 2,2'-oxybispropane. The product is filtered off and recrystallized from methanol, yielding 95.12 parts of 4-[2-(bromomethyl)-1,3-dioxolan-2-yl] benzonitrile; mp. 92.4° C.

EXAMPLE IV

Following the procedure of Example III and using equivalent amounts of the appropriate starting materials, the following dioxolanes are prepared:
2-(bromomethyl)-2-(2-naphthalenyl)-1,3-dioxolane; mp. 64° C.;
2-(bromomethyl)-2-(4-bromo-2-methylphenyl)-1,3-dioxolane; mp. 86° C.; and
2-(bromomethyl)-2-(3-nitrophenyl)-1,3-dioxolane; mp. 88° C.

EXAMPLE V

A mixture of 17.3 parts of 3-(4-bromophenoxy)-1,2-propanediol, 14.8 parts of 2-(bromomethyl)-2-(4-chloro-2-methylphenyl)-1,3-dioxolane, 4 parts of 4-methylbenzenesulfonic acid, 225 parts of methylbenzene and 40 parts of butanol is stirred and refluxed for 2 days. The reaction mixture is allowed to cool to room temperature and evaporated. Upon the addition of methanol, the product is precipitated. It is filtered off and dried, yielding 14.3 parts of A-2-(bromomethyl)-4-(4-bromophenoxymethyl)-2-(4-chloro-2-methylphenyl)-1,3-dioxolane; mp. 155° C.

EXAMPLE VI

Following the procedure of Example V and using equivalent amounts of the appropriate starting materials there are prepared:
- A-2-(bromomethyl)-2-(4-bromo-2-methylphenyl)-4-(4-bromophenoxymethyl)-1,3-dioxolane;
- A-2-(bromomethyl)-2-(3-bromo-4-methylphenyl)-4-(4-bromophenoxymethyl)-1,3-dioxolane; mp. 100° C.;
- A-4-[2-(bromomethyl)-4-(4-bromophenoxymethyl)-1,3-dioxolan-2-yl]-benzonitrile;
- A-2-(bromomethyl)-4-(4-bromophenoxymethyl)-2-(3-nitrophenyl)-1,3-dioxolane;
- A+B-4-([1,1'-biphenyl]-4-yloxymethyl)-2-(bromomethyl)-2-(2-naphthalenyl)-1,3-dioxolane; mp. 160.8° C.; and
- A-4-([1,1'-biphenyl]-4-yloxymethyl)-2-(bromomethyl)-2-(2-chloro-4-methoxyphenyl)-1,3-dioxolane.

EXAMPLE VII

A mixture of 10.2 parts of 1H-imidazole, 14.3 parts of A-2-(bromomethyl)-4-(4-bromophenoxymethyl)-2-(4-chloro-2-methylphenyl)-1,3-dioxolane, 3 parts of potassium iodide and 135 parts of N,N-dimethylacetamide is stirred and refluxed for 2 days. The reaction mixture is allowed to cool to room temperature and poured onto water. The product is extracted twice with 1,1'-oxybisethane. The combined extracts are washed twice with water and an excess of a concentrated nitric acid solution is added. The formed nitrate salt is filtered off and crystallized from a mixture of ethanol and 2,2'-oxybispropane, yielding 8.6 parts of A-1-[4-(4-bromophenoxymethyl)-2-(4-chloro-2-methylphenyl)-1,3-dioxolan-2-ylmethyl]-1H-imidazole nitrate; mp. 159.3° C.

EXAMPLE VIII

Following the procedure of Example VII and using equivalent amounts of the appropriate starting materials the following imidazole nitrate salts are prepared:
- cis-1-[2-(4-bromo-2-methylphenyl)-4-(4-bromophenoxymethyl)-1,3-dioxolan-2-ylmethyl]-1H-imidazole nitrate; mp. 164.3° C.;
- cis-1-[4-(4-bromophenoxymethyl)-2-(3-nitrophenyl)-1,3-dioxolan-2-ylmethyl]-1H-imidazole nitrate; mp. 148.8° C.;
- cis-4-[4-(4-bromophenoxymethyl)-2-(1H-imidazol-2-ylmethyl)-1,3-dioxolan-2-yl]benzonitrile nitrate; mp. 190.1° C.; and
- cis-1-[2-(3-bromo-4-methylphenyl)-4-(4-bromophenoxymethyl)-1,3-dioxolan-2-ylmethyl]-1H-imidazole nitrate; mp. 201.1° C.

EXAMPLE IX

A mixture of 7.8 parts of 1H-imidazole, 10.5 parts of A-4-([1,1'-biphenyl]-4-yloxymethyl)-2-(bromomethyl)-2-(2-chloro-4-methoxyphenyl)-1,3-dioxolane and 135 parts of N,N-dimethylacetamide is stirred and refluxed for 3 days. The reaction mixture is allowed to cool to room temperature and poured onto water. The product is extracted with 1,1'-oxybisethane. The extract is dried, filtered and evaporated. The residue is purified by column-chromatography over silica gel using trichloromethane as eluent. The pure fractions are collected and the eluent is evaporated. The residue is converted into the nitrate salt in 4-methyl-2-pentanone and 2,2'-oxybispropane. The salt is filtered off and crystallized from a mixture of acetonitrile and 2,2'-oxybispropane. The product is filtered off and dried, yielding 2 parts (16%) of cis-1-[4-([1,1'-biphenyl]-4-yloxymethyl)-2-(2-chloro-4-methoxyphenyl)-1,3-dioxolan-2-ylmethyl]-1H-imidazole nitrate; mp. 172.9° C.

EXAMPLE X

A mixture of 8.3 parts of 1H-imidazole, 11.5 parts of A+B-4-([1,1'-biphenyl]-4-yloxymethyl)-2-(bromomethyl)-2-(2-naphthalenyl)-1,3-dioxolane and 135 parts of N,N-dimethylacetamide is stirred and refluxed for 5 days. The reaction mixture is cooled and poured onto water. The product is extracted with 1,1'-oxybisethane. The extract is dried, filtered and evaporated. The residue is purified by column-chromatography over silica gel using trichloromethane as eluent. The first fraction (A-isomer) is collected and the eluent is evaporated. The residue is crystallized from 4-methyl-2-pentanone. The product is filtered off and dried, yielding 3.6 parts (33%) of cis-1-[4-([1,1'-biphenyl]-4-yloxymethyl)-2-(2-naphthalenyl)-1,3-dioxolan-2-ylmethyl]-1H-imidazole; mp. 152.6° C. The second fraction (B-isomer) is collected and the eluent is evaporated. The residue is converted into the nitrate salt in 4-methyl-2-pentanone and 2,2'-oxybispropane. The salt is filtered off and washed with acetonitrile, yielding, after drying, 3 parts (23%) of trans -1-[4-([1,1'-biphenyl]-4-yloxymethyl)-2-(2-naphthalenyl)-1,3-dioxolan-2-ylmethyl]-1H-imidazole nitrate; mp. 230.6° C.

EXAMPLE XI

A mixture of 14.6 parts of 3-([1,1'-biphenyl]-4-yloxy)-1,2-propanediol, 13.2 parts of 1-(5-chloro-2-thienyl)-2-(1H-imidazol-1-yl)-ethanone hydrochloride, 17.5 parts of 4-methylbenzenesulfonic acid, 80 parts of 1-butanol and 225 parts of dimethylbenzene is stirred and refluxed for 7 days with water-separator. The reaction mixture is cooled and diluted with 1,1'-oxybisethane. The whole is washed with a diluted sodium hydroxide solution and with water, dried, filtered and evaporated. The residue is purified by column-chromatography over silica gel using trichloromethane as eluent. The pure fractions are collected and the eluent is evaporated. The residue is converted into the nitrate salt in 4-methyl-2-pentanone and 2,2'-oxybispropane. The salt is filtered off and crystallized from a mixture of ethanol and 2,2'-oxybispropane, yielding 5.2 parts (20%) of cis-1-[4-([1,1'-biphenyl]-4-yloxymethyl)-2-(5-chloro-2-thienyl)-1,3-dioxolan-2-ylmethyl]-1H-imidazole nitrate; mp. 170° C.

EXAMPLE XII

A mixture of 9.6 parts of (1H-imidazol-1-ylmethyl)(2-thienyl)methanone, 14.6 parts of 3-([1,1'-biphenyl]-4-yloxy)-1,2-propanediol, 16 parts of 4-methylbenzenesulfonic acid, 40 parts of 1-butanol and 225 parts of dimethylbenzene is stirred and refluxed for 7 days with water-separator. The reaction mixture is cooled, washed with a diluted sodium hydroxide solution and with water, dried, filtered and evaporated. The residue is purified by column-chromatography over silica gel using trichloromethane as eluent. The first fraction (A-isomer) is collected and the eluent is evaporated. The residue is crystallized from 4-methyl-2-pentanone, yielding 6 parts of cis-1-[4-([1,1'-biphenyl]-4-yloxymethyl)-2-(2-thienyl)-1,3-dioxolan-2-ylmethyl]-1H-imidazole; mp. 149.5° C. The second fraction (B-isomer) is collected and the eluent is evaporated. The residue is crystallized from 4-methyl-2-pentanone. The product is filtered off and recrystallized from acetonitrile, yielding 1.9 parts of trans-1-[4-([1,1'-biphenyl]-4-yloxymethyl)-2-(2-thienyl)-1,3-dioxolan-2-ylmethyl]-1H-imidazole; mp. +300° C. (dec.).

EXAMPLE XIII

Following the procedure of Example (XI) and using equivalent amounts of the appropriate starting materials, there are prepared:

1-[2-(4-chloro-2-methylphenyl)-4-phenoxymethyl-1,3-dioxolan-2-ylmethyl]-1H-imidazole;
1-[2-(4-chloro-2-methylphenyl)-4-(4-methylphenoxymethyl)-1,3-dioxolan-2-ylmethyl]-1H-imidazole;
1-[2-(4-chloro-2-methylphenyl)-4-(4-methoxyphenoxymethyl)-1,3-dioxolan-2-ylmethyl]-1H-imidazole;
1-[2-(4-chloro-2-methylphenyl)-4-(4-chlorophenoxymethyl)-1,3-dioxolan-2-ylmethyl]-1H-imidazole;
1-[2-(4-chloro-2-methylphenyl)-4-(2,4-dichlorophenoxymethyl)-1,3-dioxolan-2-ylmethyl]-1H-imidazole;
1-[2-(4-bromo-2-methylphenyl)-4-phenoxymethyl-1,3-dioxolan-2-ylmethyl]-1H-imidazole;
1-[4-(4-methoxyphenoxymethyl)-2-(3-nitrophenyl)-1,3-dioxolan-2-ylmethyl]-1H-imidazole;
4-[2-(4-chlorophenoxymethyl)-2-(1H-imidazol-1-ylmethyl)-1,3-dioxolan-2-yl]benzonitrile;
1-[2-(2-chloro-4-methoxyphenyl)-4-(2,4-dichlorophenoxymethyl)-1,3-dioxolan-2-ylmethyl]-1H-imidazole;
1-[2-(2-naphthalenyl)-4-phenoxymethyl-1,3-dioxolan-2-ylmethyl]-1H-imidazole;
1-[2-(5-chloro-2-thienyl)-4-(4-methylphenoxymethyl)-1,3-dioxolan-2-ylmethyl]-1H-imidazole;
1-[4-(2,4-dichlorophenoxymethyl)-2-(2-thienyl)-1,3-dioxolan-2-ylmethyl]-1H-imidazole; and
1-[4-(4-methoxyphenoxymethyl)-2-(2-thienyl)-1,3-dioxolan-2-ylmethyl]-1H-imidazole.
1-[4-(4-bromophenoxymethyl)-2-(4-chloro-2-methylphenyl)-1,3-dioxolan-2-ylmethyl]-1H-imidazole

I claim:

1. A chemical compound selected from the group consisting of an imidazole derivative having the formula:

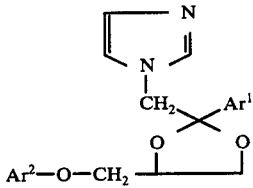

and the therapeutically acceptable acid addition salts thereof, wherein:
Ar¹ is a member selected from the group consisting of naphthalenyl, thienyl, halothienyl, nitrophenyl, cyanophenyl, lower alkyl-halophenyl and lower alkyloxy-halophenyl; and
Ar² is a member selected from the group consisting of phenyl, substituted phenyl, naphthalenyl and halonaphthalenyl, and wherein said substituted phenyl is phenyl having from 1 to 3 substituents independently selected from the group consisting of halo, lower alkyl, lower alkyloxy, cyano, phenyl and phenylmethyl.

2. A chemical compound selected from the group consisting of 1[4-(4-bromophenoxymethyl)-2-(4-chloro-2-methylphenyl)-1,3-dioxolan-2-ylmethyl]-1H-imidazole and the therapeutically acceptable acid addition salts thereof.

3. A chemical compound selected from the group consisting of cis-1-[2-(4-bromo-2-methylphenyl)-4-(4-bromophenoxymethyl)-1,3-dioxolan-2-ylmethyl]-1H-imidazole and the therapeutically acceptable acid addition salts thereof.

4. A composition for combatting the growth of a microorganism selected from the group consisting of fungus and bacterium comprising an inert carrier material and as an active ingredient an effective antifungal or antibacterial amount of a compound selected from the group consisting of an imidazole derivative having the formula:

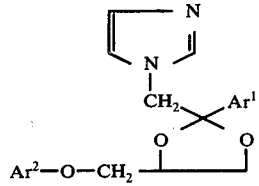

and the therapeutically active acid addition salts and stereochemical optical isomeric forms thereof, wherein:
Ar¹ is a member selected from the group consisting of naphthalenyl, thienyl, halothienyl, nitrophenyl, cyanophenyl, lower alkylhalophenyl and lower alkyloxy-halophenyl; and
Ar² is a member selected from the group consisting of phenyl, substituted phenyl, naphthalenyl and halonaphthalenyl, and wherein said substituted phenyl is phenyl having from 1 to 3 substituents independently selected from the group consisting of halo, lower alkyl, lower alkyloxy, cyano, phenyl and phenylmethyl.

* * * * *